United States Patent [19]

Sproat et al.

[11] Patent Number: 5,334,711
[45] Date of Patent: Aug. 2, 1994

[54] SYNTHETIC CATALYTIC OLIGONUCLEOTIDE STRUCTURES

[75] Inventors: Brian Sproat, Heidelberg; Angus Lamond, Wiesenbach; Giovanni Paolella, Gaiberg, all of Fed. Rep. of Germany

[73] Assignee: Europaisches Laboratorium fur Molekularbiologie (EMBL), Heidelberg, Fed. Rep. of Germany

[21] Appl. No.: 901,708

[22] Filed: Jun. 22, 1992

[30] Foreign Application Priority Data

Jun. 20, 1991 [DE] Fed. Rep. of Germany ....... 4120406
May 15, 1992 [DE] Fed. Rep. of Germany ....... 4216134

[51] Int. Cl.$^5$ ............... C07H 17/00; C07H 23/00; A01N 43/04; A61K 31/70
[52] U.S. Cl. ............... 536/24.5; 536/23.1; 536/24.3; 536/25.3; 424/2; 935/3
[58] Field of Search ............... 536/23.1, 24.3, 24.5, 536/25.3; 935/3; 514/44; 424/2

[56] References Cited

U.S. PATENT DOCUMENTS 4,469,863  9/1984  Ts'o et al. ............... 536/27

FOREIGN PATENT DOCUMENTS

0360257A2  3/1990  European Pat. Off.
0427073A2  5/1991  European Pat. Off.
0427074A2  5/1991  European Pat. Off.

OTHER PUBLICATIONS

J-P Perreault et al. (1990) Nature 344: 565–567.
Iribarren et al, Proceedings of the National Academy of Sciences of USA, Oligoribonucleotides as Antisense Probes., vol. 87, No. 19, Oct. 1990.
Hampel et al, Biochemistry, RNA Catalytic Properties of the Minimum (–)s TRSV Sequence, vol. 28, No. 12, Jun. 13, 1989.
Sproat et al, Nucleic Acids Research, New Synthetic Routes to Synthons Suitable for 2'-0-allyloligoribonucleotide Assembly., vol. 19, No. 4, 1991.
Sproat et al, Nucleic Acids Research, New Synthetic Routes to Protected Purine 2'-O-Methylriboside-3'-O-Phosphoramidites Using a Novel Alkylation Procedure., vol. 18, No. 1, 1990.
Hampel et al, Nucleic Acids Research, Catalytic RNA Model: Evidence for Helices and Sequence Requirement for Substrate RNA., vol. 18, No. 2, 1990.
Hutchins et al, Nucleic Acids Research, Self-Cleavage of Plus and Minus RNA Transcripts of Avocado Sunblotch Viroid, vol. 14, No. 9, 1986.

*Primary Examiner*—Jacqueline Stone
*Assistant Examiner*—Bruce Campell
*Attorney, Agent, or Firm*—Nikaido, Marmelstein, Murray & Oram

[57] ABSTRACT

A synthetic catalytic oligonucleotide structure and nucleotides having the general structural formula (I) contains:

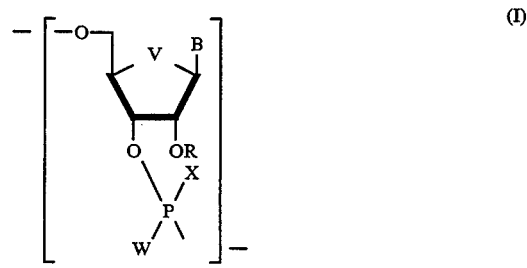

in which
B represents a nucleoside base which is in particular selected from the group comprising adenin-9-yl (A), cytosin-1-yl (C), guanin-9-yl (G), uracil-1-yl (U), uracil-5-yl ($\psi$), hypoxanthin-9-yl (I), thymin-1-yl (T) and 2-aminoadenin-9-yl,
V in each nucleotide is independently an O or a $CH_2$ group,
X and W can in each nucleotide be the same or different and are independently of each other O, S, $NH_2$, alkyl or alkoxy groups with 1 to 10, preferably with 1 to 4 carbon atoms,
R is hydrogen or a straight-chained or branched alkyl, alkenyl or alkinyl group with 1 to 10 carbon atoms which is substituted, if desired, with halogen, cyano, isocyano, nitro, amino, carboxyl, hydroxyl or/and mercapto groups, and in which in at least one of the nucleotides the residue R in formula (I) is different from hydrogen and is suitable for the cleavage of a nucleic acid target sequence.

21 Claims, No Drawings

SYNTHETIC CATALYTIC OLIGONUCLEOTIDE STRUCTURES

DESCRIPTION

The present invention concerns synthetic catalytic oligonucleotide structures which are suitable for cleaving a nucleic acid target sequence and contain modified nucleotides. In addition the invention concerns a process for cleaving a nucleic acid target sequence using synthetic catalytic modified oligonucleotide structures.

After the discovery of RNA-mediated catalysis various attempts were made to inactivate specific RNA molecules in vitro and in vivo. The discovery that hammerhead ribozymes can be used for the development of a multipurpose enzyme which is at least in vitro capable of recognizing and cleaving a given specific RNA (Haseloff and Gerlach (1988)) has proven to be of particular interest. Many interesting possibilities of using such ribozymes are based on their capability to efficiently recognize and cleave a specific RNA within a given mixture. The possibilities of using RNA enzymes range from the development of RNA restriction enzymes to the specific inactivation of genes in the cell. A particular interest in the biomedical field arises from the fact that many diseases, including many types of tumours, correlate with the expression of specific genes. The inactivation of such genes by cleaving the respective mRNA would be a possible way of controlling and finally of healing such diseases. Furthermore there is a great need for the development of antivirally active pharmaceutical agents whereby RNA enzymes could possibly be such an agent since the viral expression can be selectively blocked by cleaving the viral RNA molecules.

Previous attempts to express ribozymes in the cell by transfecting the cell with the corresponding gene have proven to be not very effective since a very high expression is necessary to inactivate the specific RNA. The direct administration of RNA molecules is probably also impossible because of the sensitivity of RNA to degradation by RNAases and their interactions with proteins.

Therefore there was a great need to develop RNA enzymes which overcome at least some of the disadvantages of the state of the art.

The object which is the basis of the invention is achieved by using a new type of nucleic acid instead of a RNA molecule which is based on artificial nucleotides with a 2′-alkoxy substituent. Such molecules are considerably more stable than native RNA molecules since they are cleaved neither by RNAases nor by DNAases and also interact less with RNA-or DNA-binding proteins (Iribarren et al., Proc. Nat. Acad. Sci. USA 87 (1990), 7747–7751). Such molecules promise to be more effective in the cellular environment than corresponding native RNA molecules. However, these modified nucleic acids are not normally effective as catalyzers, nevertheless it surprisingly turned out that their activity can be preserved when a very small number of hydroxyl residues are incorporated at specific positions on the molecule. In this process their characteristic properties, in particular stability and reduced interaction with proteins, are also surprisingly preserved.

The present invention therefore concerns a synthetic catalytic oligonucleotide structure which is suitable for cleaving a nucleic acid target sequence and contains nucleotides having the general structural formula (I):

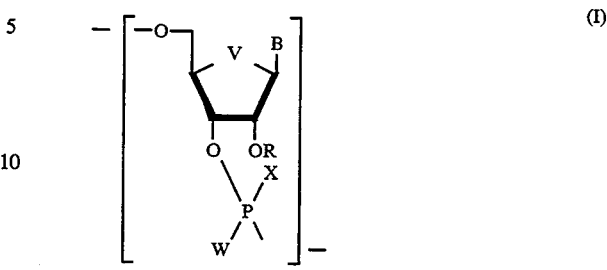

in which

B represents a nucleoside base which is in particular selected from the group comprising adenin-9-yl (A), cytosin-1-yl (C), guanin-9-yl (G), uracil-1-yl (U), uracil-5-yl ($\psi$), hypoxanthin-9-yl (I), thymin-1-yl (T) and 2-aminoadenin-9-yl, V in each nucleotide is independently an O or a $CH_2$ group, X and W can in each nucleotide be the same or different and are independently of each other O, S, $NH_2$, alkyl or alkoxy groups with 1 to 10, preferably with 1 to 4 carbon atoms, R is hydrogen or a straight-chained or branched alkyl, alkenyl or alkinyl group with 1 to 10 carbon atoms which is substituted, if desired, with halogen, cyano, isocyano, nitro, amino, carboxyl, hydroxyl or/and mercapto groups, which is characterized in that in at least one of the nucleotides the residue R in formula (I) is different from hydrogen.

B can represent any purine or pyrimidine nucleoside base. Examples of suitable purine nucleoside bases are for example adenin-9-yl, guanin-9-yl, hypoxanthin-9-yl and 2-aminoadenin-9-yl. Examples of pyrimidine nucleoside bases are for instance cytosin-1-yl, uracil1-yl, uracil-5-yl and thymin-1-yl.

In each nucleotide V is independently an O or a $CH_2$ group, preferably an O group. X and W can be the same or different in one nucleotide and independently of each other denote O, S, $NH_2$ alkyl or alkoxy groups with 1 to 10, preferably with 1 to 4 carbon atoms. It is particularly preferred that X and W are each O groups (whereby in this case one O atom would be bound via a double bond to a phosphorus and the other would be bound via a single bond and would have a negative charge).

R is hydrogen or a straight-chained or branched alkyl, alkenyl or alkinyl group with 1 to 10 carbon atoms which is substituted, if desired, with halogen (fluorine, chlorine, bromine, iodine), cyano, isocyano, nitro, amino, carboxyl, hydroxyl or/and mercapto groups. The residues R that are different from hydrogen preferably contain 1 to 6 carbon atoms. Examples of preferred residues R are methyl, ethyl, propyl, allyl, dimethylallyl, butyl or cyanomethyl residues. R is particularly preferably an alkenyl residue with 1 to 4 carbon atoms, e.g. an allyl residue.

A catalytic oligonucleotide structure according to the present invention is characterized in that the residue R in formula (I) is different from hydrogen in at least one of the nucleotides. In this connection it is preferred that the oligonucleotide structure contains as few nucleotides as possible in which R denotes hydrogen.

Such oligonucleotides are very resistant to nucleases and exhibit less interactions with nucleic acid binding proteins. On the other hand the residue R should not be different from hydrogen in all nucleotides since otherwise the oligonucleotide will no longer be catalytically active. In particular individual nucleotides are present within the catalytically active centre of the oligonucleotide according to the present invention in which the residue R represents a hydrogen atom.

The catalytically active centre of the oligonucleotide structure according to the present invention preferably has a hammerhead or a hairpin structure.

Catalytic hairpin structures are for example described in the publications of Tritz and Hampel (Biochemistry 28 (1989), 4929) and Hampel et al., Nucleic Acids Res. 18 (1990), 299–304. Such a hairpin structure contains 4 helices, two of which are formed between the substrate and the catalytic RNA. The following gives an example of a catalytic centre in the form of a RNA hairpin structure which is derived from the tobacco-ringspot virus: SEQ ID NO:3:

$N_5$ and $N_6$ are in each case nucleotides which are complementary to one another and * represents a base pairing, N' and N" either represent two nucleotide sequences which contain nucleotides which are at least partially complementary to one another so as to enable a stable base pairing between the two nucleotide sequences or N' and N" together represent a single nucleotide sequence whereby at least part of the sequence can form a double-stranded stem by base pairing between complementary nucleotides, and in which, if desired, one or several additional nucleotides N can be inserted after $N_7$ and/or $N_9$; which is characterized in that the residue R in formula (I) is different from hydrogen in at least one of the nucleotides $N_2$, $N_3$, $N_5$, $N_6$, $N_7$, $N_9$, $N_{10}$, $N_{12}$, $N_{13}$ and $N_{14}$ in formula (II).

The region $N_1$ to $N_{14}$ contains the catalytic centre of the oligonucleotide structure (II). The nucleotides denoted $(N)_x$ and $(N)_y$ are located outside the active centre and contain regions which are responsible for hybridi-

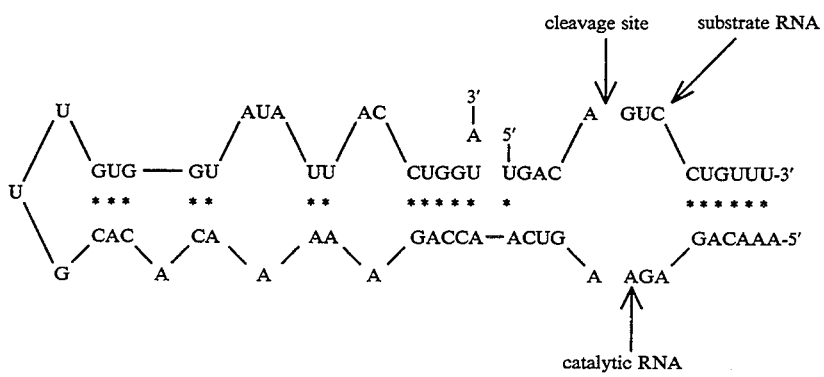

The active centre of a catalytic RNA can also have a so-called hammerhead structure (Hotchins et al., Nucleic Acids Res. 14 (1986), 3627; Kiese and Symons in: Viroids and viroid-like pathogens, J. S. Semancik, publisher (CRC Press, Bocaraton, Fla. (1987), p. 1–47)). The catalytic centre of the hammerhead structure contains 3 stems and can be formed from adjacent sequence regions of the RNA or can even be formed from regions which are separated from one another by many nucleotides.

The present invention therefore concerns a hammerhead oligonucleotide structure having the general structural formula (II)

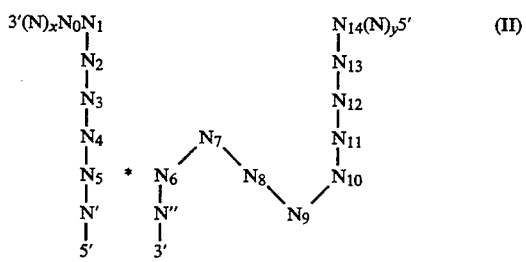

in which

N in each case represents a nucleotide according to the general structural formula (I), x and y can be the same or different and $x \geq 1$ and $y \geq 2$, zation to a specific nucleic acid target sequence. The length of these regions is such that x must be $\geq 1$ and y must be $\geq 2$. x and y are preferably $\leq 20$, larger values for x or/and y do not have any particular advantages but make the synthesis of the oligonucleotide more difficult. The oligonucleotide structure II can either be a continuous molecule or can be composed of two different molecules i.e. N' and N" either together represent a single nucleotide sequence or represent two different nucleotide sequences. It is important for the structure according to the present invention that the nucleotide sequences N' and N" contain regions which are at least partially complementary to one another that enable a stable base pairing between both nucleotide sequences. In this connection the term stable base pairing is understood to mean that the oligonucleotide structure is present as a double-stranded strand under physiological conditions at room temperature and preferably at temperatures up to 40° C.

A feature of the oligonucleotide structure according to the present invention is that the residue R in formula (I) is different from hydrogen in at least one and preferably in several of the nucleotides $N_2$, $N_3$, $N_5$, $N_6$, $N_7$, $N_9$, $N_{10}$, $N_{12}$, $N_{13}$ and $N_{14}$. In contrast the residues R in formula (I) in the nucleotides $N_1$, $N_4$, $N_8$ and $N_{11}$ are preferably hydrogen. In addition it is preferred that the nucleoside base at $N_1$ is adenin-1-yl or 2-aminoadenin-9-yl and is guanin-1-yl (or hypoxanthin-9-yl) in each of the nucleotides $N_4$, $N_8$ and $N_{11}$.

A particularly preferred subject matter of the present invention is an oligonucleotide structure having the general structural formula (III):

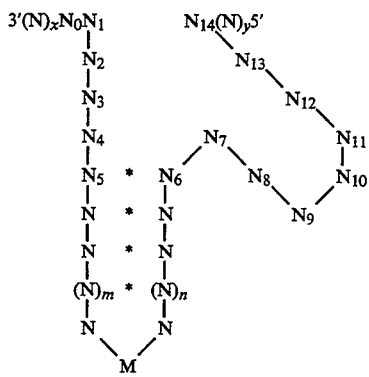

in which N, x and y are defined as in claim 3, M represents a chemical bond or denotes a nucleotide sequence $(N)_a$ in which $a \geq 1$, m and n are the same or different and in which, if desired, one or several additional nucleotides can be inserted after $N_7$ or/and $N_9$.

The residues R in formula (III) are preferably hydrogen in the nucleotides $N_1$, $N_4$, $N_8$, $N_{10}$, $N_{11}$ and $N_{12}$. The residues R in formula (III) are preferably different from hydrogen in all nucleotides apart from $N_1$, $N_4$, $N_8$, $N_{10}$, $N_{11}$ and $N_{12}$.

A preferred concrete example of an oligonucleotide according to the present invention with a hammerhead structure as the catalytic centre has a structure according to formula (II) or (III) and is characterized in that the residues V, W and X in formula (I) are O groups and the residues B and R in formula (I) or (III) have the following meanings for the nucleotides $N_1$ to $N_{14}$:

$N_1$: B=A and R=H,
$N_2$: B=A and R=allyl,
$N_3$: B=A and R=allyl,
$N_4$: B=G and R=H,
$N_5$: B=C and R=allyl,
$N_6$: B=G and R=allyl,
$N_7$: B=A and R=allyl,
$N_8$: B=G and R=H,
$N_9$: B=U and R=allyl,
$N_{10}$: B=A and R=H,
$N_{11}$: B=G and R=H,
$N_{12}$: B=U and R=H,
$N_{13}$: B=C and R=allyl,
$N_{14}$: B=U and R=allyl.

A further preferred concrete example of an oligonucleotide with a hammerhead structure as the catalytic centre is characterized in that the residues V, W and X in formula (I) are O groups except that the linkage between $N_{11}$ and $N_{12}$ is a phosphorothioate group (X=O and W=S) and that the residues B and R in formula (I) or (III) have the above-mentioned meanings for the nucleotides $N_1$ to $N_{14}$.

A further example of an oligonucleotide is characterized in that the residues V, W and X in formula (I) are O groups and that the residues B in formula (I) or (III) have the above-mentioned meanings for the nucleotides $N_1$ to $N_{14}$ and that R=H for $N_1$, $N_4$, $N_8$, $N_{10}$, $N_{11}$ and $N_{12}$, R=3,3-dimethylallyl for $N_9$ and R=allyl for $N_2$, $N_3$, $N_5$, $N_6$, $N_7$, $N_{13}$ and $N_{14}$. A further oligonucleotide differs from the latter structure only in that R=3,3-dimethylallyl for $N_3$ and R=allyl for $N_9$.

In yet another structure R=H for $N_1$, $N_4$, $N_8$, $N_{10}$, $N_{11}$ and $N_{12}$, R=cyanomethyl for $N_2$, $N_3$, $N_7$, $N_9$ and $N_{13}$ and R=allyl for $N_5$, $N_6$ and $N_{14}$ whereby the residues B have the above-mentioned concrete meanings.

In addition it may also be preferred that in the oligonucleotide structures according to the present invention one or several of the residues R are butyl in order to improve the uptake of the catalytic structures by the cell. A concrete example of this is an oligonucleotide in which R=H for $N_1$, $N_4$, $N_8$, $N_{10}$, $N_{11}$ and $N_{12}$, R=butyl for $N_5$ and $N_6$ and R=allyl for $N_2$, $N_3$, $N_7$, $N_9$, $N_{13}$ and $N_{14}$ whereby, if desired, R may also be butyl in one, several or all of the residues N that are present in formula (III) in a base-paired form (labelled by an *).

In order to additionally stabilize the oligonucleotide structures according to the present invention 3'-deoxyribonucleotides or/and 3'-O-alkylribonucleotides can be located at their free 3'-end or at their free 3'-ends. In this manner the oligonucleotide according to the present invention is protected from 3'-exonuclease degradation.

In addition the oligonucleotides according to the present invention can also contain nucleotides to stabilize their spatial configuration whose nucleoside bases are modified by a cross-linking agent. An example of such a cross-linking agent is psoralen or a psoralen derivative. In this way double-stranded oligonucleotide structures can be modified by covalent cross-linking. The production of nucleotides which are modified by a cross-linking agent is disclosed in detail in DE-A 39 28 900.

Furthermore the oligonucleotide structure according to the present invention can be linked to a prosthetic group in order to improve its uptake into the cell or/and the specific cellular localization of the oligonucleotide structure. Examples of such prosthetic groups are polyamino acids (e.g. polylysine), lipids, hormones or peptides. The linking of these prosthetic groups is usually carried out via the free 5'-ends or 3'-ends of the oligonucleotide structure according to the present invention whereby this linking is either direct or via a linker. Examples of linkers are for instance di-esters with amino or phosphate groups or with mercaptoalkoxy groups present at the terminal 5'-phosphate.

The synthesis of the oligonucleotide structures according to the present invention is carried out in a known manner from monomer units. Such monomer units usually have the general formula (V)

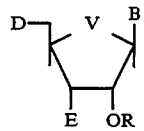

in which V, B and R are defined as in formula (I) and D and E denote reactive groups capable of forming 3'- to 5'-internucleotide bonds. Such groups are known to one skilled in the art and are described for example in B. Sproat et al., Nucleic Acids Res. 18 (1990), 41–49 as well as in summary form in E. L. Winnacker, "Gene und Klone", VCH-Verlagsgesellschaft mbH, Weinheim (Germany) (1985), in particular pages 44–49 and in Froehler and Matteucci, Tetrahedron Let. (1986), p. 469–472. Using the reactive mononucleotides having formula (V) it is possible to produce the oligonucleotide structures according to the present invention in a known manner especially on a solid phase.

The present invention additionally concerns a process for cleaving a nucleic acid target sequence using a synthetic catalytic oligonucleotide structure according to the present invention. This nucleic acid target sequence can in this case either be a part of the synthetic catalytic oligonucleotide structure itself or this nucleic acid target sequence can be a molecule which is different from the synthetic catalytic oligonucleotide structure.

If an oligonucleotide according to the present invention with a hammerhead structure having the general formula (II) is used to cleave a nucleic acid target sequence then usually an intermediate stage forms having the following structure:

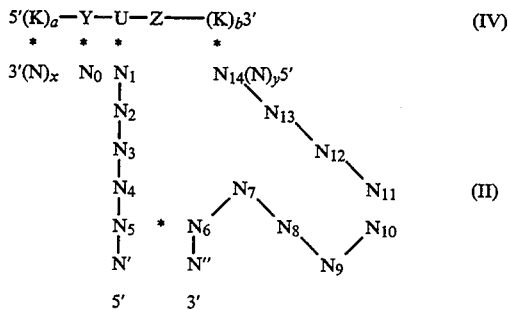

in which the symbols N, N', N'', x, y and * are defined as in claim 3, and K, Y, U and Z represent nucleotides of the nucleic acid target sequence in which U is uridine, Z is a non-modified ribonucleotide selected from the group comprising adenosine, cytidine or uridine, K and Y are any nucleotides, $a \geq 1$ and $b \geq 3$, and the cleavage of the nucleic acid target sequence takes place on the 3'-side of the nucleotide sequence YUZ and whereby, if desired, there is a chemical bond between the 5'-end of the nucleic acid target sequence (IV) and the 3'-end of the oligonucleotide (II) at $(N)_x$ or between the 3'-end of the nucleic acid target sequence (IV) and the 5'-end of the oligonucleotide (II) at $(N)_y$.

The nucleotide Y in the nucleic acid target sequence preferably represents a guanosine residue and Z preferably denotes adenosine or cytidine. The nucleic acid target sequence can be any oligo- or polynucleotide provided that Z is a non-modified ribonucleotide. The remainder of the target sequence can for example be DNA, 2'-O-alkyl-RNA or a mixed structure. The nucleic acid target sequence is, however, preferably a RNA. The cleavage specificity of the oligonucleotide according to the present invention for a certain nucleic acid target sequence can be achieved by changing the sequence of the hybridization arms of the catalytic components ($N_0(N)X$ or $(N)YN_{14}$) in such a way that they are complementary to the sequences which flank the cleavage site of the desired target sequence.

The process according to the present invention can be carried out within a living cell as well as in vitro. The cleavage is preferably carried out in the presence of a divalent cation, especially $Mg^{2+}$ and at a pH value of about 7 to 9, particularly preferably of about 8.

The present invention in addition concerns the use of an oligonucleotide structure according to the present invention for the catalytic cleavage of a nucleic acid target sequence whereby the nucleic acid target sequence is either a part of the catalytic oligonucleotide structure or represents a molecule which is different from it.

In addition the invention concerns a pharmaceutial agent which contains an oligonucleotide structure according to the present invention as the active substance, if desired, together with the usual pharmaceutical carrier agents, auxiliary agents, filling agents or/and dilution agents. The invention also concerns a process for the production of a pharmaceutical agent for antiviral therapy in humans, animals and plants whereby an oligonucleotide structure according to the present invention is used as the active substance. An example of such an antiviral therapy would be the fight against AIDS with the oligonucleotides according to the present invention (see e.g. Sarver et al., Science 247 (1990), 1222–1225).

The present invention additionally concerns a diagnostic reagent which contains an oligonucleotide structure according to the present invention as a constituent as well as a process for the production of such a diagnostic reagent. This diagnostic reagent according to the present invention can for example be used for a genetic screening procedure.

It is intended to further elucidate the invention by the following examples and the sequence protocols SEQ ID NO.1 and SEQ ID NO.2.

SEQ ID NO.1: shows the nucleotide sequence of a substrate RNA and

SEQ ID NO.2: shows the nucleotide sequence of a catalytically active ribozyme RNA

EXAMPLE 1

Oligonucleotide Synthesis, Deblocking and Purification

The synthesis of 2'-O-methylribonucleoside-3'-O-phosphoramidite building blocks was carried out according to Sproat et al. (Nucleic Acids Res. 18 (1990), 41–49). 2'-O-allylribonucleoside-3'-O-phosphoramidite building blocks were synthesized according to Sproat et al. (Nucleic Acids Res. 19 (1991), 733–738).

2'-O-[1-(2-fluorophenyl)-4-methoxypiperidin-4-yl]ribonucleoside-3'-O-phosphoramidite building blocks were synthesized according to Beijer et al. (Nucleic Acids Res. 18 (1990), 5143–5151).

The oligonucleotides were assembled according to the $\beta$-cyanoethylphosphoramadite process on controlled pore glass using a modified DNA synthesis cycle on an Applied Biosystems synthesizing apparatus. Instead of tetrazole, 5-(4-nitrophenyl)-1H-tetrazole was used as the activator for the condensation step whereby the reaction period for the condensation was increased to 12 minutes (cf. Nucleic Acids Res. 18 (1990), 41–49 and 5141–5151).

The deblocking and purification was carried out by firstly treating a carrier, to which a completely blocked oligonucleotide was bound with a solution of 25% aqueous ammonia in a sealed sterile vessel for 10 hours at 60° C. The cooled solution was then evaporated to dryness in a vacuum in a sterile vessel. The oligonucleotide crude product which still contains a 5'-terminal 5'-O-dimethoxytrityl protecting group and several 2'-O-Fpmp-protecting groups was then purified by reverse phase HPLC on a $\mu$-Bondapak $C_{18}$ column using an acetonitrile gradient in aqueous 0.1 mol/l triethylammonium acetate pH 7.0 as an eluting agent. The product peak was collected and the solvent was removed in a vacuum. The residue was resuspended in 1 ml 10% glycerol in water and the solution was centrifuged for 10 minutes. The supernatant was applied to a G15 Sephadex column (30 ml) which was eluted with sterile distilled water. The void volume of the column (about 9 ml) was discarded and a 3 ml fraction was collected which contained the partially blocked oligonucleotide. Then sterile aqueous hydrochloric acid (270 µl, 0.1 mol/l) was added by which means the pH was kept in a range from 2 to 2.5. The solution was kept at 20° to 25° C. for 20 hours in order to remove the acid-labile DMTr and Fpmp protecting groups. The solution was subsequently centrifuged for 10 minutes at 2000 rpm. The supernatant was neutralized by addition of 2 mol/l Tris-acetate (75 µl, pH 7.9). The pure completely deblocked oligonucleotide was isolated from the aqueous solution using repeated extractions with 1-butanol as described by Cathala and Brunel (Nucleic Acids Res. 18 (1990), 201). The oligonucleotide pellet was dried and dissolved in 100 µl Tris buffer (10 mmol/l, pH 7.5, 1 mmol/l EDTA).

EXAMPLE 2

Production and Labelling of Substrate RNA

Chemically synthesized substrate oligonucleotides were labelled either with $\gamma$-$^{32}$P-ATP and kinase or with RNA ligase and $^{32}$P-pCp according to the standard procedures proposed by the manufacturers for the respective enzymes.

As an alternative to this, RNA was also synthesized by transcription with SP6-RNA polymerase after linearizing the respective templates with suitable restriction enzymes. The RNA molecules were labelled by incorporating $\alpha$-$^{32}$P-UTP in the transcript. The conditions for the transcription were as follows:

40 mmol/l Tris, pH 7.5
6 mmol/l MgCl$_2$
2 mmol/l spermidine
10 mmol/l dithiothreitol
500 mmol/l nucleoside triphosphates (A, C, G)
100 µmol/l UTP
10 µCi $\alpha$-$^{32}$P-UTP
10 U/µl SP6-polymerase
20 U/µl RNAse inhibitor (human placenta)

After a two hour incubation at 37° C. the DNA used as a template was digested with RNAse-free DNAse. RNA was separated by gel electrophoresis on 6% polyacrylamide gels (acrylamide:bis-acrylamide 1:30) in the presence of 7 mol/l urea. RNA bands were eluted by diffusion and RNA was isolated by ethanol precipitation. The determination of activity was carried out in a 10 µl reaction mixture which contained substrate RNA (10 nM to 1 µM), 50 mM Tris pH 7.5, 20 mM MgCl$_2$, 0.01 to 10 pMol ribozyme. This mixture was incubated for 60 minutes at 50° C. The cleavage products were separated on a 7% polyacrylamide gel in the presence of 7 M urea.

EXAMPLE 3

Determination of the Activity of Different Modified Catalytic Oligonucleotides

A 17 nucleotide long chemically synthesized oligoribonucleotide based on the EDB exon of human fibronectin mRNA was used as the target sequence. The sequence (SEQ ID NO.1) was as follows:

5'-r[UACACAGUCACAGGGCU]

The ribozyme used to cleave this sequence had the nucleotide sequence (SEQ ID NO.2) shown in the following:

5'-r[GCCCUG<u>UCUGAUGAGUCCGUGAGGAC GAAACUGUGU</u>]

This sequence is denoted E0. The underlined regions mark the nucleotides $N_{14}$ to $N_6$ or $N_5$ to $N_0$ according to formula (III). In addition the following analogues of E0 (with an identical base composition) were synthesized:

E1: R=H for $N_1$, $N_4$, $N_8$, $N_{10}$, $N_{11}$ and $N_{12}$; R=allyl for all the other N's.

E2: R=H for $N_1$, $N_4$, $N_8$, $N_{10}$ and $N_{11}$; R=allyl for all the other N's.

E3: R=H for $N_1$, $N_4$, $N_8$, $N_{10}$, $N_{11}$ and $N_{12}$; the connection between $N_{11}$ and $N_{12}$ is a phosphorothioate group (i.e. X=O and W=S according to formula (I)); R=allyl for all the other N's.

E4: R=H for $N_1$, $N_4$, $N_8$, $N_{10}$, $N_{11}$ and $N_{12}$; R=3,3-dimethylallyl for $N_9$ and R=allyl for all the other N's.

E5: R=H for $N_1$, $N_4$, $N_8$, $N_{10}$, $N_{11}$ and $N_{12}$; R=3,3-dimethylallyl for $N_3$ and R=allyl for all the other N's.

E6: R=H for $N_1$, $N_4$, $N_8$, $N_{10}$, $N_{11}$ and $N_{12}$; R=butyl for $N_5$ and $N_6$ as well as for all the other 6 N's (UCC and GGA), that form a base-paired region. R=allyl for all the other N's.

E7: R=H for $N_1$, $N_4$, $N_8$, $N_{10}$, $N_{11}$ and $N_{12}$; R=cyanomethyl for $N_2$, $N_3$, $N_7$, $N_9$ and $N_{13}$; R=allyl for all the remaining N's.

The test to determine the cleavage activity was carried out in a reaction volume of 10 µl which contained the substrate RNA (10 nmol/l to 1 µmol/l), 50 mmol/l Tris pH 7.5, 20 mmol/l MgCl$_2$ and 0.01 to 10 pmol ribozyme. The reaction mixture was incubated for 60 minutes at 50° C. The cleavage products were separated by polyacrylamide gel electrophoresis in the presence of 7 mol/l urea.

The reaction kinetics were determined by measuring the amount of $^{32}$P-radioactively labelled substrate for a cleavage duration of 1.5, 10 and 15 minutes at 50° C. The substrate concentrations were as follows: 25, 50, 100, 250 nmol/l; the ribozyme concentration was between 4 nmol/l and 20 nmol/l. The samples were preheated and the reaction was started by addition of ribozyme. After the predetermined reaction period the reaction was stopped by addition of 2 volumes 20 mmol/l EDTA. The products were separated by polyacrylamide-urea gel electrophoresis and quantitatively analyzed with a Molecular Dynamics phosphorus imager.

In the following Table 1 the relative activity and RNase sensitivity of the above-listed catalytic oligonucleotides E0, E1, E2, E3, E4, E5, E6 and E7 are stated.

TABLE 1

| Catalytic structure | Relative activity | RNase A sensitivity |
|---|---|---|
| E0 | 1 | 1 |
| E1 | 0.2 | 0.01 |
| E2 | <0.05 | stable |
| E3 | 0.1 | 0.001 |
| E4 | ca. 0.2 | 0.01 |
| E5 | ca. 0.2 | 0.01 |
| E6 | ca. 0.2 | 0.01 |

TABLE 1-continued

| Catalytic structure | Relative activity | RNase A sensitivity |
|---|---|---|
| E7 | ca. 0.2 | 0.01 |

SEQ ID NO.1:

Nucleic acid (RNA):
single-stranded
linear
length: 17

UACACAGUCA CAGGGCU                17

SEQ ID NO.2:

Nucleic acid (RNA):
single-stranded
linear
length: 36

GCCCUGUCUG AUGAGUCCGU GAGGACGAAA CUGUGU    36

We claim:
1. An oligonucleotide structure with a catalytically active center which has a hammerhead structure, having the general structural formula (II):

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:1:

UACACAGUCA CAGGGCU                                                17

( 2 ) INFORMATION FOR SEQ ID NO:2:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:2:

GCCCUGUCUG AUGAGUCCGU GAGGACGAAA CUGUGU                           36

( 2 ) INFORMATION FOR SEQ ID NO:3:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:3:

AAACAGAGAA GUCAACCAGA AAAACACACG UUGUGGUAUA UUACCUGGUU GACAGUCCUG   60
UUU                                                                63

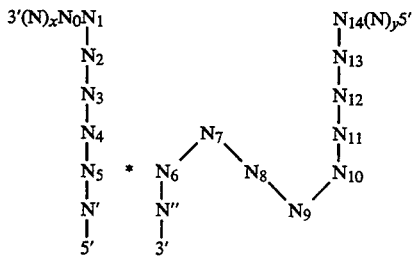
(II)

wherein
x and y can be the same or different and $x \geq 1$ and $y \geq 2$, $N_5$ and $N_6$ are in each case nucleotides which are complementary to one another and * represents a base pairing, N' and N" either represent two nucleotide sequences which contain nucleotides which are at least partially complementary to one another so as to enable a stable base pairing between the two nucleotide sequences or N' and N" together represent a single nucleotide sequence whereby at least part of the sequence can form a double-stranded stem at least part of the sequence can form a double-stranded stem by base pairing between complementary nucleotides, and in which, at least one additional nucleotide N can be inserted after $N_7$ or/and $N_9$;

the residue R in formula (I) is different from hydrogen in at least one of the nucleotides $N_2$, $N_3$, $N_5$, $N_6$, $N_7$, $N_9$, $N_{10}$, $N_{12}$, $N_{13}$ and $N_{14}$ in formula (II), and N in each case represents a nucleotide according to the general structural formula (I)

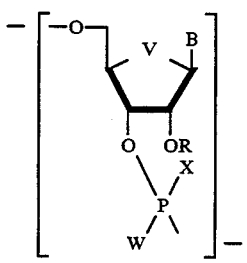
(I)

wherein
B represents a nucleoside base which is selected from the group consisting of adenin-9-yl (A), cytosin-1-yl (C), guanin-9-yl (G), uracil-1-yl (U), uracil-5-yl (ψ), hypoxanthin-9-yl (I), thymin-1-yl (T) and 2-aminoadenin-9-yl, V in each nucleotide is independently an O or a $CH_2$ group, X and W can in each nucleotide be the same different and are independently O, S, $NH_2$, alkyl or alkoxy groups with 1 to 10 carbon atoms, and R is hydrogen or a straight-chained or branched alkyl, alkenyl or alkinyl group with 1 to 10 carbon atoms which is unsubstituted or substituted with halogen, cyano, isocyano, nitro, amino, carboxyl, hydroxyl or/and mercapto groups.

2. Oligonucleotide structure as claimed in claim 1 wherein
the residues R in formula (I) are hydrogen in the nucleotides $N_1$, $N_4$, $N_8$ and $N_{11}$.

3. Oligonucleotide structure as claimed in claim 1, wherein
the residues V, W and X in formula (I) and O groups.

4. Oligonucleotide structure as claimed in claim 1, wherein
the residues R in formula (I) which are different from hydrogen contain 1 to 6 carbon atoms.

5. Oligonucleotide structure as claimed in claims 4, wherein
the residues R in formula (I) which are different from hydrogen are selected from the group comprising methyl, ethyl, propyl, allyl, dimethylallyl, butyl or cyanomethyl residues.

6. Oligonucleotide structure as claimed in claim 1 having the general structural formula (III):

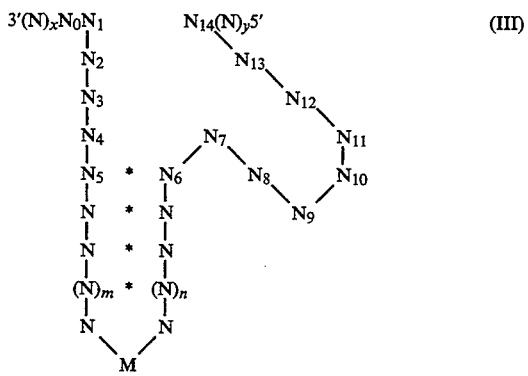
(III)

in which N, x and y are as previously defined M represents a chemical bond or denotes a nucleotide sequence $(N)_a$, whereby $a \geq 1$, m and n are the same or different and, if desired, one or several additional nucleotides can be inserted after $N_7$ or/and $N_9$.

7. Oligonucleotide structure as claimed in claim 6 wherein
the residues R in formula (III) are hydrogen in the nucleotides $N_1$, $N_4$, $N_8$, $N_{10}$, $N_{11}$ and $N_{12}$.

8. Oligonucleotide structure as claimed in claim 6, wherein
the residues R in formula (III) are different from hydrogen in all nucleotides apart from $N_1$, $N_4$, $N_8$, $N_{10}$, $N_{11}$ and $N_{12}$.

9. Oligonucleotide structure as claimed in claim 1, wherein
the residues V, W and X in formula (I) are O groups and the residues B and R in formula (I) or (III) have the following meanings for the nucleotides $N_1$ to $N_{14}$:

$N_1$: B=A and R=H,
$N_2$: B=A and R=allyl,
$N_3$: B=A and R=allyl,
$N_4$: B=G and R=H,
$N_5$: B=C and R=allyl,
$N_6$: B=G and R=allyl,
$N_7$: B=A and R=allyl,
$N_8$: B=G and R=H,
$N_9$: B=U and R=allyl,
$N_{10}$: B=A and R=H,
$N_{11}$: B=G and R=H,
$N_{12}$: B=U and R=H,
$N_{13}$: B=C and R=allyl,
$N_{14}$: B=U and R=allyl.

10. Oligonucleotide structure as claimed in claim 1, wherein the residues V, W and X in formula (I) are O groups with the exception that the linkage between $N_{11}$ and $N_{12}$ is a phosphorothioate group (X=O and W=S) and the residues B and R in formula (I) or (III) have the meaning according to claim 12 for the nucleotides $N_1$ to $N_{14}$.

11. Oligonucleotide structure as claimed in claim 1, wherein the residues V, W and X in formula (I) are O groups and the residues B in formula (I) or (III) have the meaning according to claim 12 for the nucleotides $N_1$ to $N_{14}$ and R=H for $N_1$, $N_4$, $N_8$, $N_{10}$, $N_{11}$ and $N_{12}$, R=3,3-dimethylallyl for $N_9$ and R=allyl for $N_2$, $N_3$, $N_5$, $N_6$, $N_7$, $N_{13}$ and $N_{14}$.

12. Oligonucleotide structure as claimed in claim 1, wherein the residues V, W and X in formula (I) are O groups and the residues B in formula (I) or (III) have the meaning according to claim 12 for the nucleotides $N_1$ to $N_{14}$ and R=H for $N_1$, $N_4$, $N_8$, $N_{10}$, $N_{11}$ and $N_{12}$, R=3,3-dimethylallyl for $N_3$ and R=allyl for $N_2$, $N_5$, $N_6$, $N_7$, $N_9$, $N_{13}$ and $N_{14}$.

13. Oligonucleotide structure as claimed in claim 1, wherein the residues V, W and X in formula (I) are O groups and the residues B in formula (I) or (III) have the meaning according to claim 12 for the nucleotides $N_1$ to $N_{14}$ and R=H for $N_1$, $N_4$, $N_8$, $N_{10}$, $N_{11}$ and $N_{12}$, R=cyanomethyl for $N_2$, $N_3$, $N_7$, $N_9$ and $N_{13}$ and R=allyl for $N_5$, $N_6$ and $N_{14}$.

14. Oligonucleotide structure as claimed in claim 1, wherein the residues V, W and X in formula (I) are O groups and the residues B in formula (I) or (III) have the meaning according to claim 12 for the nucleotides $N_1$ to $N_{14}$ and R=H for $N_1$, $N_4$, $N_8$, $N_{10}$, $N_{11}$ and $N_{12}$, R=butyl for $N_5$ and $N_6$ and R=allyl for $N_2$, $N_3$, $N_7$, $N_9$, $N_{13}$ and $N_{14}$ whereby, if desired, R=butyl in one or several of the residues N that are present in a base-paired form in formula (III).

15. Oligonucleotide structure as claimed in claim 1, wherein it is linked to a prosthetic group selected from poly-amino acids, lipids, hormones or peptides in order to improve the uptake into the cell or/and the specific cellular localization of the oligonucleotide structure.

16. Diagnostic reagent, wherein it contains an oligonucleotide structure as claimed in claim 1 as a constituent.

17. An oligonucleotide structure with a catalytically active center which has a hammerhead structure, having the general structural formula (II):

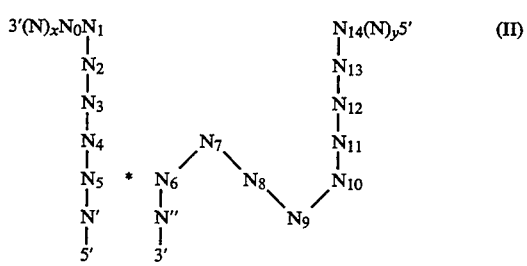

wherein x and y can be the same or different and $x \geq 1$ and $y \geq 2$, $N_5$ and $N_6$ are in each case nucleotides which are complementary to one another and * represents a base pairing, N′ and N″ either represent two nucleotide sequences which contain nucleotides which are at least partially complementary to one another so as to enable a stable base pairing between the two nucleotide sequences or N′ and N″ together represent a single nucleotide sequence whereby at least part of the sequence can form a double-stranded stem by base pairing between complementary nucleotides, wherein, at least one additional nucleotide N can be inserted after $N_7$ or/and $N_9$; and N in each case represents a nucleotide according to the general structural formula (I)

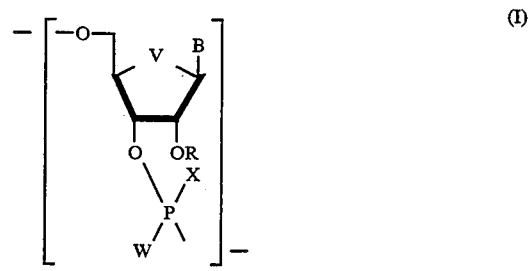

in which B represents a nucleoside base which is in particular selected from the group consisting of adenin-9-yl (A), cytosin-1-yl (C), guanin-9-yl (G), uracil-1-yl (U), uracil-5-yl (ψ), hypoxanthin-9-yl (I), thymin-1-yl (T) and 2-aminoadenin-9-yl, $N_1$: B=A or an A-analogue
$N_2$: B=A or an A-analogue
$N_3$: B=A or an A-analogue
$N_4$: B=G or an G-analogue
$N_7$: B=A or an A-analogue
$N_8$: B=G or an G-analogue
$N_9$: B=U
$N_{10}$: B=A or an A-analogue
$N_{11}$: B=G or an G-analogue
$N_{12}$: B=U
$N_{13}$: B=C
$N_{14}$: B=U V in each nucleotide is independently an O or a $CH_2$ group, X and W can in each nucleotide be the same or different and are independently O, S, $NH_2$, alkyl or alkoxy groups with 1 to 10 carbon atoms, and R is hydrogen or a straight-chained or branched alkyl, alkenyl or alkinyl group with 1 to 10 carbon atoms which is unsubstituted or substituted with halogen, cyano, isocyano, nitro, amino, carboxyl, hydroxyl or/and mercapto groups, wherein in at least one of the nucleotides the residue R in formula (I) is different from hydrogen.

18. An oligonucleotide structure according to claim 1 wherein B in nucleotide $N_1$ is selected from the group consisting of adenin-9-yl (A) and 2-aminoadenin-9-yl and B in nucleotides $N_4$, $N_8$, and $N_{11}$ is guanin-9-yl (G).

19. An oligonucleotide structure according to claim 1, wherein 3′deoxyribonucleotides and/or 3′-O-alkyl-ribonucleotides are present at a free 3′ end of the oligonucleotide structure.

20. A pharmaceutical agent comprising the oligonucleotide according to claim 1 in combination with a pharmaceutically acceptable carrier.

21. An oligonucleotide structure according to claim 1, wherein X and W can in each nucleotide be the same or different and are independently O, S, $NH_2$, alkyl or alkoxy groups with 1 to 4 carbon atoms.

* * * * *